United States Patent [19]

Barker et al.

[11] 4,116,669
[45] Sep. 26, 1978

[54] HERBICIDAL TETRAHYDROFURAN DERIVATIVES

[75] Inventors: Michael D. Barker; Eirlys R. Barker, both of Maidstone, England

[73] Assignee: Shell Oil Company, Houston, Tex.

[21] Appl. No.: 849,567

[22] Filed: Nov. 8, 1977

[30] Foreign Application Priority Data

Nov. 10, 1976 [GB] United Kingdom ............... 46771/76

[51] Int. Cl.$^2$ ..................... A01N 9/28; C07D 307/12; C07D 307/28; C07D 307/94
[52] U.S. Cl. ..................................... 71/88; 260/347.2; 260/347.8
[58] Field of Search ............... 71/88; 260/347.2, 347.8

[56] References Cited

U.S. PATENT DOCUMENTS

| | | | |
|---|---|---|---|
| 2,153,135 | 4/1939 | Dickey et al. | 260/347.8 X |
| 2,277,359 | 3/1942 | Schirm et al. | 260/347.8 X |
| 2,561,307 | 7/1951 | Copenhaver | 260/347.8 X |
| 2,895,965 | 7/1959 | Eugster et al. | 260/347.8 X |
| 3,940,502 | 2/1976 | Winter et al. | 260/347.8 X |

OTHER PUBLICATIONS

Cleophax et al, Chemical Abstracts, vol. 66 (1967) 55,689z.

*Primary Examiner*—Richard L. Raymond

[57] ABSTRACT

Certain benzyloxymethyltetrahydrofuran derivatives are useful as herbicides.

14 Claims, No Drawings

HERBICIDAL TETRAHYDROFURAN DERIVATIVES

The present invention relates to novel tetrahydrofuran derivatives to be specified hereinafter, as well as to a method of their preparation. The tetrahydrofuran derivatives according to the present invention have interesting herbicidal properties. The present invention therefore also relates to herbicidal compositions comprising a carrier or a surface-active agent or both a carrier and a surface-active agent and at least one tetrahydrofuran derivative to be specified hereinafter. The present invention also relates to a method of eradicating or controlling weeds infesting cereal crops at a locus by applying a herbicidally effective amount of a tetrahydrofuran derivative or a composition containing a tetrahydrofuran derivative according to the present invention.

The novel compounds according to the present invention are tetrahydrofuran derivatives of the general formula:

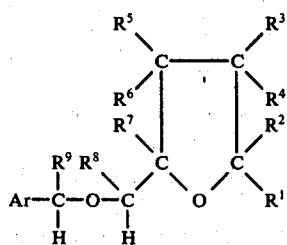

wherein $R^1$ and $R^2$ each individually represents a hydrogen atom, a halogen atom, an optionally substituted alkyl, cycloalkyl or aryl group or $R^1$ and $R^2$ together represent an alkylene moiety, $R^3$, $R^4$, $R^5$ and $R^6$ each individually represents a hydrogen atom, a halogen atom having an atomic number of from 9 to 35, inclusive, an optionally substituted alkyl, alkoxy, thioalkoxy or aryl group or one of $R^3$ and $R^4$ and one of $R^5$ and $R^6$ together represent a carbon-carbon bond or an epoxide moiety; $R^7$ represents a hydrogen atom or optionally substituted alkyl group; $R^8$ and $R^9$ each individually represents a hydrogen atom or an optionally substituted alkyl group; and Ar represents an optionally substituted phenyl group.

Preferred tetrahydrofuran derivatives are those of formula I, wherein $R^1$ and $R^2$ each individually represents a hydrogen atom, an alkyl group of up to 6 carbon atoms or a substituted or unsubstituted phenyl group; or together represent an alkylene moiety of up to 6 carbon atoms; $R^3$, $R^4$, $R^5$ and $R^6$ each individually represents a hydrogen atom, a halogen atom or an alkyl group of up to 6 carbon atoms or one of $R^3$ and $R^4$ and one of $R^5$ and $R^6$ together represent a carbon-carbon bond; $R^7$ represents a hydrogen atom or an alkyl group of up to 6 carbon atoms; $R^8$ and $R^9$ each individually represents a hydrogen atom or an alkyl group of up to 6 carbon atoms; and Ar represents a phenyl group or a phenyl group substituted by one or more halogen atoms or alkyl or alkoxy groups of up to 6 carbon atoms.

Particularly preferred tetrahydrofuran derivatives are those of formula I, wherein $R^1$ and $R^2$ each individually represents a hydrogen atom, a methyl group, or $R^1$ and $R^2$ together represent a pentamethylene moiety; $R^3$, $R^4$, $R^5$ and $R^6$ each individually represents a hydrogen atom or one of $R^3$ and $R^4$ and one of $R^5$ and $R^6$ together represent a carbon-carbon bond; $R^7$ represents a hydrogen atom, a methyl or ethyl group, preferably an ethyl group; $R^8$ and $R^9$ each individually represents a hydrogen atom; and Ar represents a phenyl group or a phenyl group substituted with a 2-methyl-, 2-fluoro- or a 2,6-dichloro group.

Suitable substituents referred to hereinabove comprise halogen atoms having an atom number of from 9 to 35, inclusive, especially chlorine or fluorine atoms; and alkyl, alkoxy or thioalkoxy group, the alkyl portions of which each contain from 1 to 6 carbon atoms, an aryl or aryloxy group, the aryl portions of which each contain from 6 to 12 carbon atoms, preferably a phenyl group, or a cycloalkyl group containing 3 to 6 carbon atoms.

The tetrahydrofuran derivatives according to the present invention can exist in several geometric forms, such as cis-configuration, trans-configuration as well as in optically active forms. These forms as well as mixtures thereof are within the scope of the present invention. The various isomers of the tetrahydrofuran derivatives of formula I may have different herbicidal activities. Thus, one may prefer to resolve an isomer mixture to recover a more herbicidally active isomer or to prepare the more active form for use in the invention.

The tetrahydrofuran derivatives according to the present invention may be prepared by reacting a compound of formula:

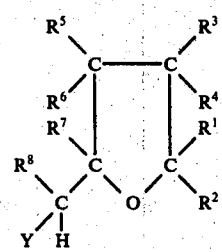

with a compound of formula:

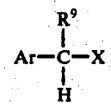

wherein $R^1$-$R^9$ and Ar have the meanings as defined hereinbefore and one of X and Y represents a halogen atom and the other a group OZ, wherein Z represents a hydrogen atom or an alkali or alkaline earth atom.

The reaction is preferably carried out by reacting a compound of formula II, wherein Y represents a hydroxy group with a compound of formula III, wherein X represents a halogen atom in the presence of a base, such as sodium hydride, if desired in the presence of an aromatic solvent, such as benzene or toluene. The reactions are suitably carried out under reflux conditions.

The compounds of formula II can be prepared by methods known in the art.

As mentioned hereinbefore, the tetrahydrofuran derivatives according to the present invention are of interest as herbicides. The invention therefore includes herbicidal compositions comprising a carrier and/or a surface-active agent together with at least one tetrahydrofuran derivative according to formula I. The present invention also includes a method of eradicating or controlling weeds in crops at a locus by applying to a locus a herbicidally active amount of a tetrahydrofuran derivative according to formula I or a composition containing as active ingredient at least one tetrahydrofuran derivative according to formula I.

The term "carrier" as used herein means a solid or fluid material with which the active ingredient is mixed or formulated to facilitate its application to the plant, seed, soil or other object to be treated, or its storage, transport or handling. Any of the carrier materials or surface-active agents usually applied in formulating pesticides may be used in the compositions according to the invention, and suitable examples of these are to be found, for example, in British patent specification No. 1,293,546.

The compositions of the invention may be formulated as wettable powders, dusts, granules, solutions, emulsifiable concentrates, emulsions, suspensions, concentrates or aerosols. Wettable powders are usually compounded to contain 25-75%w of toxicant and usually contain, in addition to solid carrier, 3-10%w of a dispersing agent and, where necessary, up to 10%w of stabilizer(s) and/or additives such as penetrants or stickers. Dusts are usually formulated as a dust concentrate having a similar composition to that of a wettable powder but without a dispersant, and are diluted in the field with further solid carrier to give a composition usually containing 0.5-10%w of toxicant. Granules are usually prepared to have a size between 0.15 and 1.68 mm, and may be manufactured by agglomeration or impregnation techniques. Generally, granules will contain 0.5-25%w of toxicant and, where necessary, up to 10%w of additives, such as stabilizers, slow-release modifiers and binding agents. Emulsifiable concentrates usually contain, in addition to the solvent and, where necessary, co-solvent, 10-50% w/v of toxicant, 2-20% w/v of emulsifiers and, where necessary, up to 20% w/v of appropriate additives, such as stabilizers, penetrants and corrosion inhibitors. Suspension concentrates are compounded so as to obtain a stable, non-sedimenting, flowable product and usually contain 10-75%w of toxicant, 0.5-15%w of dispersing agent(s), 0.1-10%w of suspending agents, such as protective colloids and thioxotropic agents, and, where necessary, up to 10%w of appropriate additives, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as anti-freeze agents for water.

Aqueous dispersions and emulsions, for example compositions obtained by diluting a wettable powder or an emulsifiable concentrate according to the invention with water, also lie within the scope of the present invention. The said emulsions may be of the water-in-oil or of the oil-in-water type, and may have a thick 'mayonaise'-like consistency.

The compositions according to the invention may also contain other ingredients, for example those mentioned in British patent specification No. 1,293,546 and/or other pesticidally active compounds, such as insecticides, acaricides, herbicides or fungicides which are compatible with the other ingredients in the composition.

The invention is further illustrated in the following Examples. The structures of the compounds prepared were confirmed by elemental and N.M.R. analysis.

EXAMPLE 1

Preparation of 2,5,5-trimethyl-2-(2-methylbenzyloxymethyl) tetrahydrofuran 2,5,5-Trimethyl-2-hydroxymethyl tetrahydrofuran (1.6 g) was added slowly to a stirred suspension of sodium hydride (0.4 g of 80% dispersion in oil) in dry toluene (55 ml). After the addition the mixture was heated under reflux for 1 hour. 2-Methylbenzyl chloride (1.8 g) was added and the mixture heated under reflux overnight. The cooled mixture was washed with water (x2) and dried and the solvent was removed under reduced pressure. The product was purified by chromatography on silica using methylene dichloride as eluent. Yield 80%.

Analysis: Calculated for $C_{16}H_{24}O_2$: C, 77.4; H, 9.7%. Found: C, 77.1; H, 10.1%.

EXAMPLE 2

Preparation of 2,5,5-trimethyl-2-benzyloxymethyl tetrahydrofuran

Hydrogen was added to a solution of 2,5,5-trimethyl-2-benzyloxymethyldihydrofuran (4.7 g) in ethanol (100 ml) under vigorous stirring in the presence of 5% Pd/(BaSO$_4$) at room temperature for 6 hours. After filtration the solvent was removed and the product was purified by chromatography on silica using acetone/petrol as eluent. Yield 57%.

Analysis: Calculated for $C_{15}H_{22}O_2$: C, 76.0; H, 9.4%. Found: C, 77.2; H, 9.5%.

EXAMPLES 3-23

Further compounds were prepared whose physical characteristics and analyses are set out in Table I.

EXAMPLE 24

Herbicidal activity

To evaluate their herbicidal activity, the compounds according to the invention were tested using as a representative range of plants: — maize, Zea mays (Mz); rice, Oryza sativa (R); barnyard grass, Echinochloa crusgalli (BG); oat, Avena sativa (O); linseed, Linum usitatissimum (L); mustard, Sinapsis alba (M); sugar beet, Beta vulgaris (SB) and soya bean, Glycine max (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which seedling plants of the above species were growing, was drenched with a liquid formulation containing a compound of the invention, and in the foliar spray tests the seedling plants were sprayed with such a formulation.

TABLE I

| Example | Compound | Analysis (%) |
|---|---|---|
| 3 | 2,5-dimethyl-2-benzyloxymethyl | Calculated for $C_{14}H_{20}O_2$ : C 76.5; H 9.1 |

TABLE I-continued

| Example | Compound | Analysis (%) |
|---|---|---|
|  | tetrahydrofuran | Found : C 76.0; H 9.2 |
| 4 | 2-benzyloxymethyl-5-phenyl tetrahydrofuran | Calculated for $C_{18}H_{20}O_2$ : C 80.6; H 7.5<br>Found : C 81.0; H 7.5 |
| 5 | 2,5,5-trimethyl-2-benzyloxymethyl dihydrofuran | Calculated for $C_{15}H_{20}O_2$ : C 77.6; H 8.6<br>Found : C 75.5; H 9.1 |
| 6 | 2,5,5-trimethyl-2-(2,6-dichloro-benzyloxymethyl) tetrahydrofuran | Calculated for $C_{15}H_{20}Cl_2O_2$: C 59.4; H 6.6<br>Found : C 59.8; H 6.7 |
| 7 | 2,5,5-trimethyl-2-(2-fluorobenzyl-oxymethyl) tetrahydrofuran | Calculated for $C_{15}H_{21}FO_2$ : C 71.4; H 8.3<br>Found : C 71.7; H 8.6 |
| 8 | 2-methyl-2-benzyloxymethyl-dihydro-furan-5-spirocyclohexane | Calculated for $C_{18}H_{24}O_2$ : C 79.4; H 8.8<br>Found : C 79.4; H 9.1 |
| 9 | 2-methyl-2-benzyloxymethyl-tetra-hydrofuran-5-spirocyclohexane | Calculated for $C_{18}H_{26}O_2$ : C 78.8; H 9.5<br>Found : C 79.1; H 9.5 |
| 10 | 2-methyl-2-(2-methylbenzyloxymethyl)-tetrahydrofuran-5-spirocyclohexane | Calculated for $C_{19}H_{28}O_2$ : C 79.2; H 9.7<br>Found : C 79.0; H 9.9 |
| 11 | 2-methyl-2-(2-fluorobenzyloxymethyl)-tetrahydrofuran-5-spirocyclohexane | Calculated for $C_{18}H_{25}FO_2$ : C 74.0; H 8.6<br>Found : C 74.2; H 8.6 |
| 12 | 2-methyl-2-(2,6-dichlorobenzyloxy-methyl)-tetrahydrofuran-5-spiro-cyclohexane | Calculated for $C_{18}H_{24}Cl_2O_2$: C 63.0; H 7.0<br>Found : C 63.2; H 7.2 |
| 13 | 2,5,5-trimethyl-2-benzyloxymethyl-3,4-epoxy tetrahydrofuran | Calculated for $C_{15}H_{20}O_3$ : C 72.6; H 8.1<br>Found : C 73.4; H 8.4 |
| 14 | 2-ethyl-5,5-dimethyl-2-benzyloxy-methyl dihydrofuran | Calculated for $C_{16}H_{22}O_2$ : C 78.0; H 8.9<br>Found : C 78.1; H 9.5 |
| 15 | 2-ethyl-5,5-dimethyl-2-benzyloxy-methyl tetrahydrofuran | Calculated for $C_{16}H_{24}O_2$ : C 77.4; H 9.7<br>Found : C 77.1; H 10.1 |
| 16 | 2-ethyl-5,5-dimethyl-2-(2,6-dichloro-benzyloxymethyl) tetrahydrofuran | Calculated for $C_{16}H_{22}Cl_2O_2$: C 60.6; H 6.9; Cl 22.4<br>Found : C 61.3; H 7.4; Cl 22.2 |
| 17 | 2-ethyl-2-benzyloxymethyl-dihydro-furan-5-spirocyclohexane | Calculated for $C_{19}H_{26}O_2$ : C 79.7; H 9.1<br>Found : C 79.9; H 9.3 |
| 18 | 2-ethyl-2-(2-fluorobenzyloxymethyl)-tetrahydrofuran-5-spirocyclohexane | Calculated for $C_{19}H_{27}O_2F$ : C 74.5; H 8.8<br>Found : C 79.9; H 9.3 |
| 19 | 2-ethyl-2-benzyloxymethyl-tetra-hydrofuran-5-spirocyclohexane | Calculated for $C_{19}H_{28}O_2$ : C 79.2; H 9.7<br>Found : C 79.2; H 10.0 |
| 20 | 2-ethyl-2-(2-methylbenzyloxymethyl)-tetrahydrofuran-5-spirocyclohexane | Calculated for $C_{20}H_{30}O_2$ : C 79.5; H 9.9<br>Found : C 79.3; H 10.2 |
| 21 | 2-ethyl-2-(2,6-dichlorobenzyloxy-methyl)-tetrahydrofuran-5-spiro-cyclohexane | Calculated for $C_{19}H_{26}O_2Cl_2$: C 63.9; H 7.3<br>Found : C 64.4; H 7.7 |
| 22 | 2-ethyl-2-(2-bromobenzyloxymethyl)-tetrahydrofuran-5-spirocyclohexane | Calculated for $C_{19}H_{27}O_2Br$: C 62.1; H 7.4<br>Found : C 62.1; H 7.6 |
| 23 | 2,5,5-trimethyl-4-ethyl-2-benzyloxy-methyl tetrahydrofuran | Calculated for $C_{17}H_{26}O_2$ : C 77.9; H 9.9<br>Found : C 77.6; H 10.3 |

The soil used in the tests was a steam-sterilized, modified John Innes Compost mixture in which half the peat, by loose bulk, had been replaced by vermiculite.

The formulations used in the tests were prepared by diluting with water and solutions of the compounds in acetone containing 0.4% by weight of an alkylphenol-/ethylene oxide condensate available under the trade name TRITON X-155. In the soil spray and foliar spray tests the acetone solutions were diluted with an equal volume of water and the resulting formulations applied at two dosage levels corresponding to 5 and 1 kilogram(s) of active material per hectare respectively in a volume equivalent to 400 liters per hectare. In the soil drench tests one volume of the acetone solution was diluted to 155 volumes with water and the resulting formulation applied at one dosage level equivalent to 10 kilograms of active material per hectare in a volume equivalent to approximately 3,000 liters per hectare.

In the pre-emergence tests untreated sown soil and in the post-emergence tests untreated soil bearing seedlings plants were used as controls.

The herbicidal effects of the compounds were assessed visually seven days after spraying the foliage and drenching the soil and eleven days after spraying the foliage and drenching the soil and eleven days after spraying the soil, and were recorded on a 0-9 scale. A rating 0 indicates no effect on the treated plants, a rating 2 indicates a reduction in fresh weight of stem and leaf of the plants of approximately 25%, a rating 5 indicates a reduction of approximately 55%, a rating 9 indicates a reduction of 95%, etc.

The results of the tests are set out in Table II below.

TABLE II

| Compound | Dose kg/ha | Post emergence (plants) | | | | | | | | Foliar spray | | | | | | | Seeds Pre-emergence | | | | | |
|---|---|---|---|---|---|---|---|---|---|---|---|---|---|---|---|---|---|---|---|---|---|---|
| | | Soil drench | | | | | | | | | | | | | | | | | | | | |
| | | Mz | R | BG | O | L | M | SB | S | Mz | R | BG | O | L | M | SB | S | Mz | R | BG | O | L | M | SB | S |
| 2,5,5-trimethyl-2-(2-benzyloxymethyl) tetrahydrofuran | 5 | 8 | 8 | 8 | 8 | 0 | 5 | 0 | 5 | 5 | 0 | 5 | 7 | 6 | 6 | 5 | 4 | 8 | 9 | 9 | 8 | 0 | 5 | 2 | 7 |
| 2,5,5-trimethyl-2-benzyloxymethyl tetrahydrofuran | 1 5 | 8 | 7 | 8 | 8 | 6 | 4 | 5 | 5 | 0 7 | 0 3 | 2 9 | 4 7 | 3 6 | 3 6 | 1 5 | 1 6 | 5 8 | 8 9 | 9 9 | 4 9 | 0 4 | 0 5 | 0 0 | 2 3 |
| 2,5-dimethyl-2-benzyloxymethyl tetrahydrofuran | 1 5 | 7 | 6 | 7 | 0 | 5 | 2 | 5 | 0 | 4 5 | 0 1 | 7 8 | 5 5 | 4 5 | 0 0 | 2 2 | 0 0 | 7 6 | 9 9 | 9 9 | 8 8 | 0 8 | 3 8 | 0 7 | 2 |
| 2-benzyloxymethyl-5-phenyl-tetrahydrofuran | 1 5 | 6 | 5 | 7 | 0 | 0 | 0 | 0 | 0 | 0 4 | 0 0 | 0 7 | 0 0 | 0 8 | 0 7 | 0 6 | 0 5 | 0 5 | 6 7 | 8 9 | 0 3 | 8 4 | 4 2 | 0 7 | 0 |
| 2,5,5-trimethyl-2-benzyloxymethyl dihydrofuran | 1 5 | 8 | 7 | 8 | 6 | 7 | 6 | 5 | 1 | 0 6 | 0 0 | 2 8 | 0 4 | 5 4 | 1 4 | 0 5 | 2 4 | 5 8 | 2 9 | 9 9 | 1 9 | 4 6 | 1 3 | 1 4 | 0 1 |
| 2,5,5-trimethyl-2-(2,6-dichlorobenzyloxymethyl)tetrahydrofuran | 1 | 8 | 3 | 7 | 8 | 0 | 3 | 7 | 3 | 2 7 | 0 0 | 7 8 | 0 8 | 0 5 | 0 7 | 0 6 | 0 5 | 3 9 | 8 8 | 9 9 | 6 5 | 0 7 | 0 7 | 2 6 | 0 4 |
| 2,5,5-trimethyl-2-(2-fluorobenzyloxymethyl)-tetrahydrofuran | 5 | 9 | 7 | 9 | 8 | 6 | 7 | 3 | 6 | 4 | 0 | 3 | 4 | 0 | 4 | 3 | 2 | 4 | 6 | 9 | 2 | 1 | 6 | 4 | 2 |
| 2-methyl-2-benzyloxymethyl-dihydrofuran-5-spirocyclohexane | 1 5 | 8 | 5 | 7 | 2 | 0 | 2 | 0 | 0 | 0 3 | 0 2 | 0 8 | 0 5 | 0 5 | 0 8 | 0 5 | 0 5 | 9 | 7 7 | 9 9 | 7 6 | 3 7 | 5 6 | 8 5 | 8 |
| 2-methyl-2-benzyloxymethyl-tetrahydrofuran-5-spirocyclohexane | 1 5 | 8 | 6 | 9 | 8 | 4 | 7 | 4 | 2 | 1 6 | 0 2 | 1 8 | 0 8 | 5 8 | 3 9 | 0 8 | 2 6 | 4 9 | 2 9 | 9 9 | 3 7 | 1 8 | 1 7 | 0 6 | 0 8 |
| 2-methyl-2-(2-methyl-benzyloxymethyl)-tetrahydrofuran-5-spirocyclohexane | 1 5 | 8 | 4 | 8 | 7 | 3 | 3 | 5 | 2 | 5 6 | 0 4 | 6 9 | 5 8 | 6 8 | 6 8 | 3 6 | 4 5 | 8 9 | 8 7 | 9 9 | 5 8 | 5 5 | 4 7 | 0 6 | 1 6 |
| 2-methyl-2-(2-fluorobenzyloxymethyl)-tetrahydrofuran-5-spirocyclohexane | 5 | 7 | 2 | 9 | 6 | 2 | 0 | 4 | 4 | 3 | 0 | 7 | 5 | 7 | 7 | 1 | 3 | 7 | 5 | 9 | 6 | 0 | 6 | 5 | 2 |
| 2-methyl-2-(2,6-dichlorobenzyloxymethyl)-tetrahydrofuran-5-spirocyclohexane | 1 | 5 | 0 | 7 | 6 | 0 | 0 | 0 | 2 | 4 | 0 | 0 | 8 | 8 | 8 | 8 | 8 | 9 | 9 | 9 | 8 | 8 | 6 | 6 | 8 |
| 2-methyl-2-(2,6-dichlorobenzyloxymethyl)-tetrahydrofuran-5-spirocyclohexane | 1 | 5 | 0 | 7 | 7 | 0 | 0 | 0 | 2 | 7 | 0 | 8 | 3 | 8 | 5 | 5 | 5 | 4 | 8 | 9 | 6 | 5 | 5 | 6 | 2 |
| 2,5,5-trimethyl-2-benzyloxymethyl-3,4-epoxy-tetrahydrofuran | 5 | 7 | 4 | 7 | 7 | 2 | 3 | 4 | 0 | 2 | 0 | 7 | 7 | 7 | 7 | 7 | 6 | 8 | 5 | 9 | 6 | 2 | 0 | 6 | 7 |
| 2-ethyl-5,5-dimethyl-2-benzyloxymethyl-tetrahydrofuran | 1 5 | 9 | 7 | 9 | 6 | 5 | 5 | 5 | 6 | 0 9 | 0 4 | 4 9 | 0 5 | 0 6 | 3 7 | 0 6 | 0 3 | 1 9 | 2 9 | 9 9 | 2 9 | 0 5 | 0 4 | 0 4 | 0 |
| 2-ethyl-5,5-dimethyl-2-benzyloxymethyl-dihydrofuran | 1 5 | 9 | 7 | 9 | 8 | 6 | 6 | 5 | 7 | 8 9 | 2 5 | 8 9 | 4 8 | 1 7 | 2 7 | 5 8 | 2 7 | 8 9 | 9 9 | 9 9 | 7 9 | 0 7 | 1 6 | 2 5 | 0 5 |
| 2-ethyl-5,5-dimethyl-2-(2,6-dichlorobenzyloxymethyl)-tetrahydrofuran | 1 5 | 8 | 6 | 9 | 8 | 0 | 6 | 7 | 3 | 8 8 | 2 3 | 8 9 | 4 8 | 2 8 | 4 7 | 2 7 | 4 7 | 9 9 | 9 9 | 9 9 | 9 8 | 5 8 | 4 6 | 3 6 | 4 8 |
| 2-ethyl-2-benzyloxymethyl-dihydrofuran-5-spirocyclohexane | 1 5 | 8 | 6 | 9 | 6 | 0 | 0 | 0 | 0 | 6 | 0 | 8 | 6 | 7 | 5 | 6 | 6 | 9 9 | 9 9 | 9 9 | 7 6 | 6 7 | 6 6 | 4 5 | 3 0 |
| 2-ethyl-2-(2-fluorobenzyloxymethyl)-tetrahydrofuran | 1 5 | 8 | 5 | 9 | 7 | 3 | 0 | 0 | 0 | 6 | 0 | 8 | 0 | 5 | 5 | 2 | 3 | 9 | 7 | 9 | 4 | 7 | 6 | 7 | 7 |

TABLE II-continued

| Compound | Dose kg/ha | Post emergence (plants) Soil drench | | | | | | | | Foliar spray | | | | | | | | Seeds Pre-emergence | | | | | | | |
|---|---|---|---|---|---|---|---|---|---|---|---|---|---|---|---|---|---|---|---|---|---|---|---|---|---|
| | | Mz | R | BG | O | L | M | SB | S | Mz | R | BG | O | L | M | SB | S | Mz | R | BG | O | L | M | SB | S |
| furan-5-spirocyclohexane 2-ethyl-2-benzyloxymethyl-tetrahydrofuran-5-spiro-cyclohexane | 1 | 7 | 6 | 9 | 8 | 4 | 5 | 5 | 2 | 9 | 0 | 9 | 6 | 7 | 6 | 0 | 3 | 9 | 7 | 8 | 4 | 7 | 6 | 7 | 7 |
| | 5 | | | | | | | | | 9 | 5 | 9 | 8 | 7 | 7 | 3 | 7 | 9 | 9 | 9 | 7 | 8 | 7 | 4 | 8 |
| 2-ethyl-2-(2-methylbenzyloxymethyl)-tetrahydrofuran-5-spirocyclohexane | 1 | 6 | 0 | 9 | 8 | 2 | 3 | 4 | 1 | 9 | 1 | 8 | 5 | 6 | 5 | 0 | 2 | 9 | 9 | 9 | 6 | 6 | 6 | 3 | 5 |
| | 5 | | | | | | | | | 8 | 4 | 8 | 7 | 6 | 6 | 2 | 6 | 8 | 9 | 9 | 6 | 5 | 5 | 6 | 7 |
| 2-ethyl-2-(2,6-dichlorobenzyloxymethyl)-tetrahydrofuran-5-spirocyclohexane | 1 | 3 | 0 | 8 | 5 | 0 | 0 | 2 | 0 | 4 | 2 | 7 | 5 | 6 | 5 | 0 | 3 | 8 | 8 | 9 | 5 | 4 | 5 | 3 | 6 |
| | 5 | | | | | | | | | 3 | 0 | 8 | 3 | 6 | 7 | 2 | 5 | 7 | 2 | 9 | 4 | 4 | 5 | 5 | 1 |
| 2-ethyl-2-(2-bromobenzyloxymethyl)-tetrahydrofuran-5-spirocyclohexane | 1 | 4 | 0 | 7 | 6 | 0 | 0 | 0 | 0 | 8 | 0 | 8 | 4 | 7 | 7 | 0 | 4 | 7 | 5 | 9 | 4 | 5 | 6 | 4 | 5 |
| | 5 | | | | | | | | | 7 | 0 | 9 | 7 | 5 | 5 | 3 | 3 | 9 | 9 | 9 | 9 | 7 | 5 | 4 | 0 |
| 2,5,5-trimethyl-4-ethyl-2-benzyloxymethyl-tetrahydrofuran | 1 | 8 | 5 | 9 | 8 | 0 | 3 | 6 | 0 | 4 | 0 | 6 | 1 | 1 | 0 | 0 | 2 | 9 | 7 | 9 | 3 | 4 | 0 | 2 | 0 |

What we claim is:
1. A tetrahydrofuran derivative of the formula

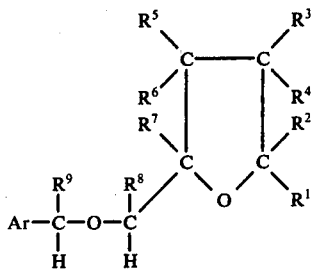

wherein $R^1$ and $R^2$ each individually represents a hydrogen atom, a methyl group, or $R^1$ and $R^2$ together represent a pentamethylene moiety; $R^3$, $R^4$, $R^5$, and $R^6$ each individually represents a hydrogen atom or one of $R^3$ and $R^4$ and one of $R^5$ and $R^6$ together represent a carbon-carbon bond; $R^7$ represents an ethyl group; $R^8$ and $R^9$ each individually represents a hydrogen atom; and Ar represents a phenyl group or a phenyl group substituted with a 2-methyl-, 2-fluoro- or a 2,6-dichloro group.

2. 2-Ethyl-5,5-dimethyl-2-benzyloxymethyl-tetrahydrofuran.

3. 2-Ethyl-5,5-dimethyl-2-(2,6-dichlorobenzyloxymethyl)-tetrahydrofuran.

4. 2-Ethyl-2-benzyloxymethyl-tetrahydrofuran-5-spirocyclohexane.

5. 2,5,5-Trimethyl-2-benzyloxymethyl-tetrahydrofuran.

6. 2-Ethyl-5,5-dimethyl-2-benzyloxymethyl-dihydrofuran.

7. 2-Ethyl-2-benzyloxymethyl-dihydrofuran-5-spirocyclohexane.

8. 2,5,5-Trimethyl-4-ethyl-2-benzyloxymethyl-tetrahydrofuran.

9. A herbicidal composition comprising as active ingredient a herbicidally effective amount of a tetrahydrofuran derivative according to claim 3, and at least one carrier or a surface-active agent.

10. A herbicidal composition according to claim 9 wherein the tetrahydrofuran derivative is selected from 2-ethyl-5,5-dimethyl-2-benzyloxymethyl-tetrahydrofuran, 2-ethyl-5,5-dimethyl-2-(2,6-dichlorobenzyloxymethyl)-tetrahydrofuran, 2-ethyl-2-benzyloxymethyl-tetrahydrofuran-5-spirocyclohexane, 2,5,5-trimethyl-2-benzyloxymethyl-tetrahydrofuran, 2-ethyl-5,5-dimethyl-2-benzyloxymethyl-dihydrofuran, 2-ethyl-2-benzyloxymethyl-dihydrofuran-5-spirocyclohexane, 2,5,5-trimethyl-4-ethyl-2-benzyloxymethyl-tetrahydrofuran.

11. A method of eradicating or controlling weeds infesting cereal crops at a locus by applying a herbicidally active amount of a tetrahydrofuran derivative of the formula

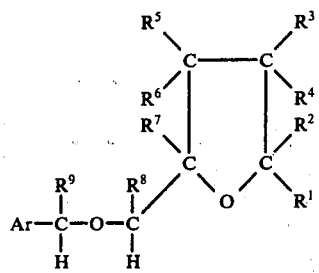

wherein $R^1$ and $R^2$ each individually represents a hydrogen atom, an alkyl group of up to 6 carbon atoms or a phenyl group; or together represent an alkylene moiety of up to 6 carbon atoms; $R^3$, $R^4$, $R^5$ and $R^6$ each individually represents a hydrogen atom, a halogen atom or an alkyl group of up to 6 carbon atoms or one of $R^3$ and $R^4$ and one of $R^5$ and $R^6$ together represent a carbon-carbon bond; $R^7$ represents a hydrogen atom or an alkyl group of up to 6 carbon atoms; $R^8$ and $R^9$ each individually represents a hydrogen atom or an alkyl group of up to 6 carbon atoms; and Ar represents a phenyl group or a phenyl group substituted by one or more halogen atoms or alkyl or alkoxy groups of up to 6 carbon atoms.

12. A method according to claim 11, wherein in the tetrahydrofuran derivative $R^1$ and $R^2$ each individually represents a hydrogen atom, methyl group or $R^1$ and $R^2$ together represent a pentamethylene moiety; $R^3$, $R^4$, $R^5$ and $R^6$ each individually represents a hydrogen atom or one of $R^3$ and $R^4$ and one of $R^5$ and $R^6$ together represents a carbon-carbon bond; $R^7$ represents a hydrogen atom, a methyl group or an ethyl group; $R^8$ and $R^9$ each individually represents a hydrogen atom; and Ar represents a phenyl group or a phenyl group substituted with a 2-methyl, 2-fluoro-, or a 2,6-dichloro group.

13. A method according to claim 12 wherein in the tetrahydrofuran derivative $R^7$ is an ethyl group.

14. A method according to claim 12 wherein the tetrahydrofuran derivative is selected from 2-ethyl-5,5-dimethyl-2-benzyloxymethyl-tetrahydrofuran, 2-ethyl-5,5-dimethyl-2-(2,6-dichlorobenzyloxymethyl)-tetrahydrofuran, 2-ethyl-2-benzyloxymethyl-tetrahydrofuran-5-spirocyclohexane, 2,5,5-trimethyl-2-benzyloxymethyl-tetrahydrofuran, 2-ethyl-5,5-dimethyl-2-benzyloxymethyl-dihydrofuran, 2-ethyl-2-benzyloxymethyl-dihydrofuran-5-spirocyclohexane, 2,5,5-trimethyl-4-ethyl-2-benzyloxymethyl-tetrahydrofuran.

* * * * *

UNITED STATES PATENT AND TRADEMARK OFFICE
CERTIFICATE OF CORRECTION

PATENT NO. : 4,116,669

DATED : September 26, 1978

INVENTOR(S) : Michael D. Barker and Eirlys R. Barker

It is certified that error appears in the above—identified patent and that said Letters Patent are hereby corrected as shown below:

Claim 9, line 3, change "3" to -- 1 --.

Signed and Sealed this

Twenty-seventh Day of February 1979

[SEAL]

Attest:

RUTH C. MASON
Attesting Officer

DONALD W. BANNER
Commissioner of Patents and Trademarks